US011547632B2

(12) United States Patent
Carter et al.

(10) Patent No.: US 11,547,632 B2
(45) Date of Patent: Jan. 10, 2023

(54) MEDICAL VIAL HOLDER APPARATUS AND METHOD

(71) Applicant: TBM Medical Solutions, Inc., Simi Valley, CA (US)

(72) Inventors: David Peter Carter, Oxfordshire (GB); Simon Edward Morse, Oxfordshire (GB)

(73) Assignee: TBM Medical Solutions, Inc., Simi Valley, CA (US)

( * ) Notice: Subject to any disclaimer, the term of this patent is extended or adjusted under 35 U.S.C. 154(b) by 0 days.

(21) Appl. No.: 17/631,471

(22) PCT Filed: Aug. 1, 2020

(86) PCT No.: PCT/US2020/044686
§ 371 (c)(1),
(2) Date: Jan. 29, 2022

(87) PCT Pub. No.: WO2021/022244
PCT Pub. Date: Feb. 4, 2021

(65) Prior Publication Data
US 2022/0313555 A1    Oct. 6, 2022

Related U.S. Application Data

(60) Provisional application No. 62/881,930, filed on Aug. 1, 2019.

(51) Int. Cl.
*A61J 1/16*      (2006.01)
*A61J 1/20*      (2006.01)
*F16B 2/18*      (2006.01)

(52) U.S. Cl.
CPC ............... *A61J 1/16* (2013.01); *A61J 1/2055* (2015.05); *A61J 1/2065* (2015.05); *A61J 1/2096* (2013.01); *F16B 2/185* (2013.01)

(58) Field of Classification Search
CPC .......... A61J 1/16; A61J 1/2056; A61J 1/2065; A61J 1/2096; F16B 2/185
See application file for complete search history.

(56) References Cited

U.S. PATENT DOCUMENTS 2,122,722 A *   7/1938   O'Neill ............... A61M 5/1782
                                                                                    604/414
3,314,635 A      4/1967   Frye
(Continued)

*Primary Examiner* — Anita M King
(74) *Attorney, Agent, or Firm* — Lance M. Pritikin

(57) ABSTRACT

Embodiments of a medical vial holder apparatus and system are disclosed. A main body has a mount engagement portion and a vial engagement portion. A facing wall is attached to the vial engagement portion thereby defining a vial retention cavity therebetween. A lever element is mounted to the main body for pivotal movement between a grip position and a release position. The lever element has a grip portion with a vial engagement face. A grip distance is defined between the vial engagement face and the facing wall. Movement of the lever element from the release position toward the grip position reduces the grip distance. Movement of the lever element from the grip position toward the release position increases the grip distance. The lever element is biased toward the grip position. A plurality of the apparatuses are adjustably mountable in line with one another by way of their mount engagement portions.

33 Claims, 19 Drawing Sheets

(56) References Cited

U.S. PATENT DOCUMENTS

| | | | |
|---|---|---|---|
| 3,982,716 | A | 9/1976 | Trees |
| 4,005,844 | A | 2/1977 | Richmond |
| 5,013,155 | A | 5/1991 | Rybak |
| 5,316,732 | A | 5/1994 | Golukhov et al. |
| 5,669,502 | A | 9/1997 | Ong et al. |
| 5,775,485 | A | 7/1998 | Dierking |
| 5,924,659 | A | 7/1999 | Babcock |
| 5,975,470 | A * | 11/1999 | Casey ................. A61M 5/1782 248/176.1 |
| 6,070,761 | A * | 6/2000 | Bloom .................... A61J 3/002 141/330 |
| D622,377 | S | 8/2010 | Jackson |
| 8,302,640 | B2 | 11/2012 | Molina et al. |
| D799,717 | S | 10/2017 | Bohm et al. |
| 9,878,098 | B1 | 1/2018 | Opland |
| 10,441,711 | B2 | 10/2019 | Brehm et al. |
| 10,646,403 | B2 * | 5/2020 | Lizari Illarramendi .. A61J 1/16 |
| D904,627 | S | 12/2020 | Black et al. |
| 2002/0124905 | A1 | 9/2002 | Draughn et al. |
| 2011/0253251 | A1 | 10/2011 | Mudd |
| 2012/0101407 | A1 | 4/2012 | Chan |
| 2019/0151851 | A1 | 5/2019 | Kauffmann |
| 2020/0222283 | A1 * | 7/2020 | Lizari Illarramendi .. A61J 1/16 |

\* cited by examiner

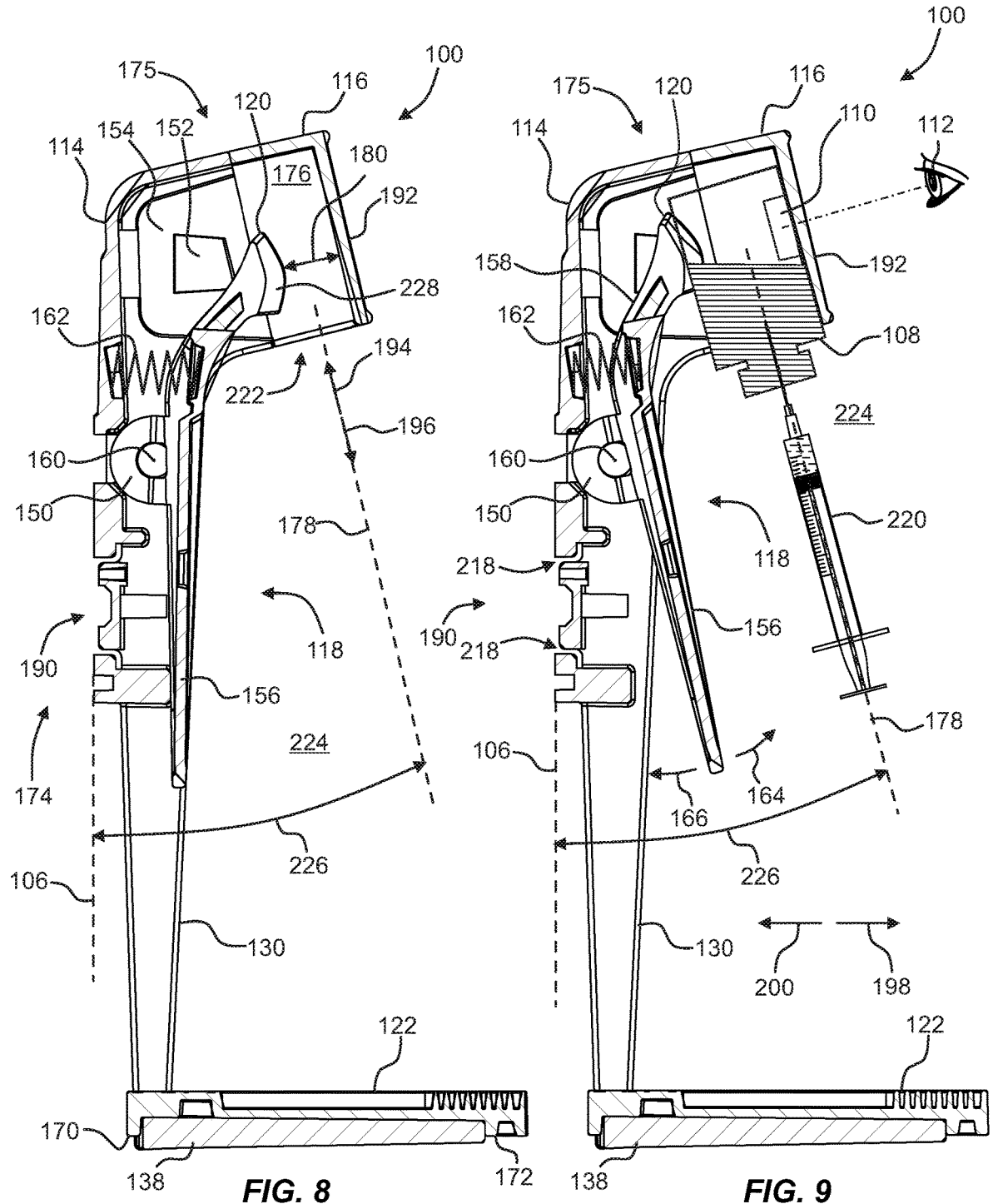

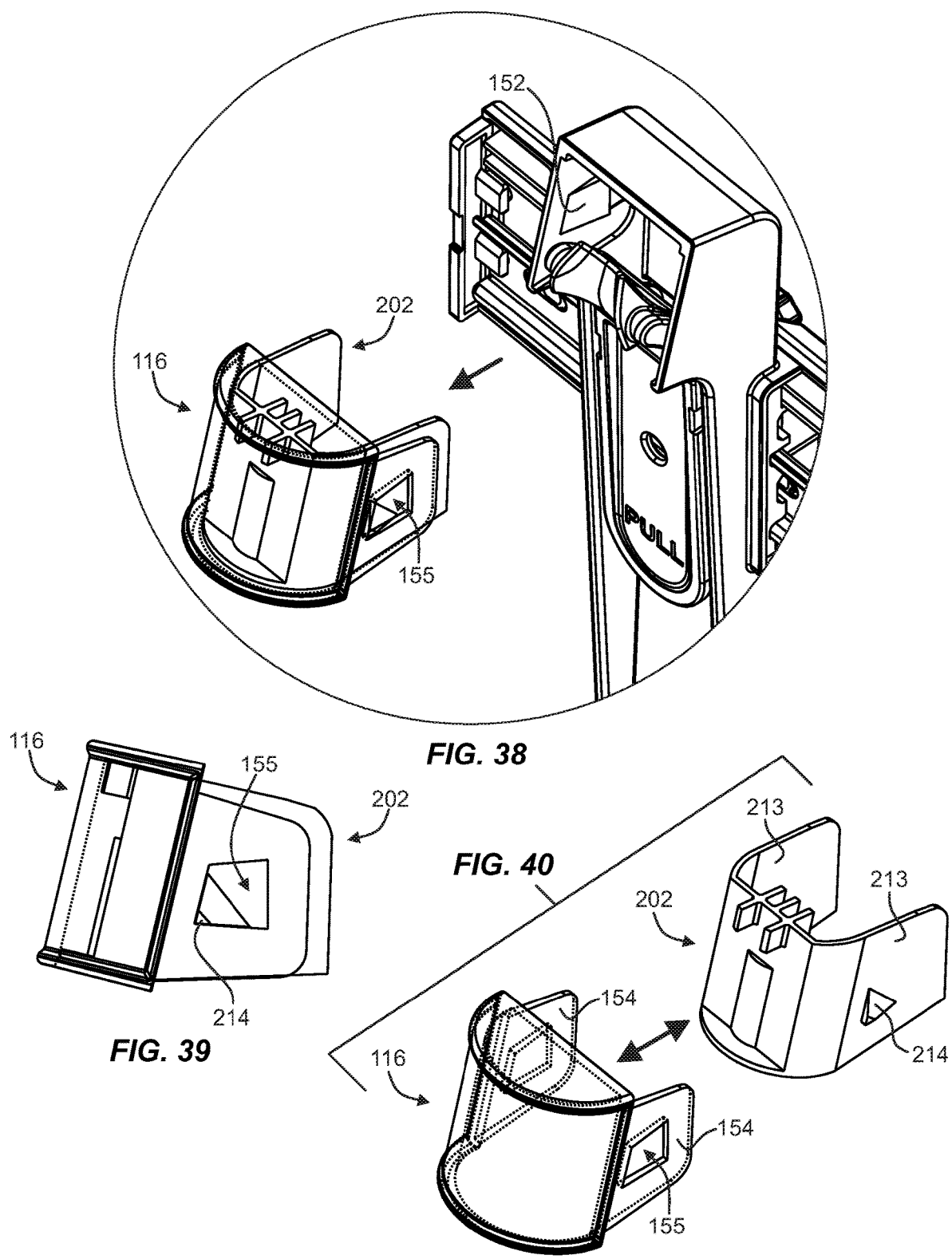

MEDICAL VIAL HOLDER APPARATUS AND METHOD

RELATED APPLICATIONS

This application claims the benefit of U.S. Provisional Application No. 62/881,930 filed Aug. 1, 2019, the contents of which are incorporated by this reference in their entireties for all purposes as if fully set forth herein.

TECHNICAL FIELD

The present disclosure relates generally to devices and methods for holding medical vials in inverted positions for extraction of medicinal fluids therefrom using a syringe.

BACKGROUND

Conventional expedients for capturing and retaining a medical vial in an inverted position exist in the prior art. However, such conventional devices may require excessive dexterity on the part of the user, may be costly and complex to assemble, and may lack features which would otherwise help a user operate such a device more quickly, effectively and safely while under pressure in a medical treatment environment.

SUMMARY

Certain deficiencies of the prior art are overcome by the provision of embodiments of a medical vial holder apparatus and system as disclosed herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 8 is a diagrammatic cross-sectional view taken along lines 8-8 in FIG. 6, illustrating the lever element in a grip position with the grip distance minimized;

FIG. 9 is a diagrammatic cross-sectional view similar to that of FIG. 8, but wherein an inverted medical vial is shown grippingly retained within the vial retention cavity of the apparatus with the label on the vial being viewable through the window element from a viewpoint outward of the window element, the lever element having been moved to a gripping position with an increased grip distance;

FIG. 38 is a diagrammatic partial perspective view of an example medical vial holder system, wherein the window element and the vial size adaptor are shown being disassembled from the vial engagement portion of the main body;

FIG. 39 is a diagrammatic side view of the combined window element and vial size adaptor shown in FIG. 38; and FIG. 40 is a diagrammatic perspective view of the disassembly of the vial size adaptor and window element of FIG. 39.

DETAILED DESCRIPTION OF THE PREFERRED EMBODIMENTS

Figure 1:
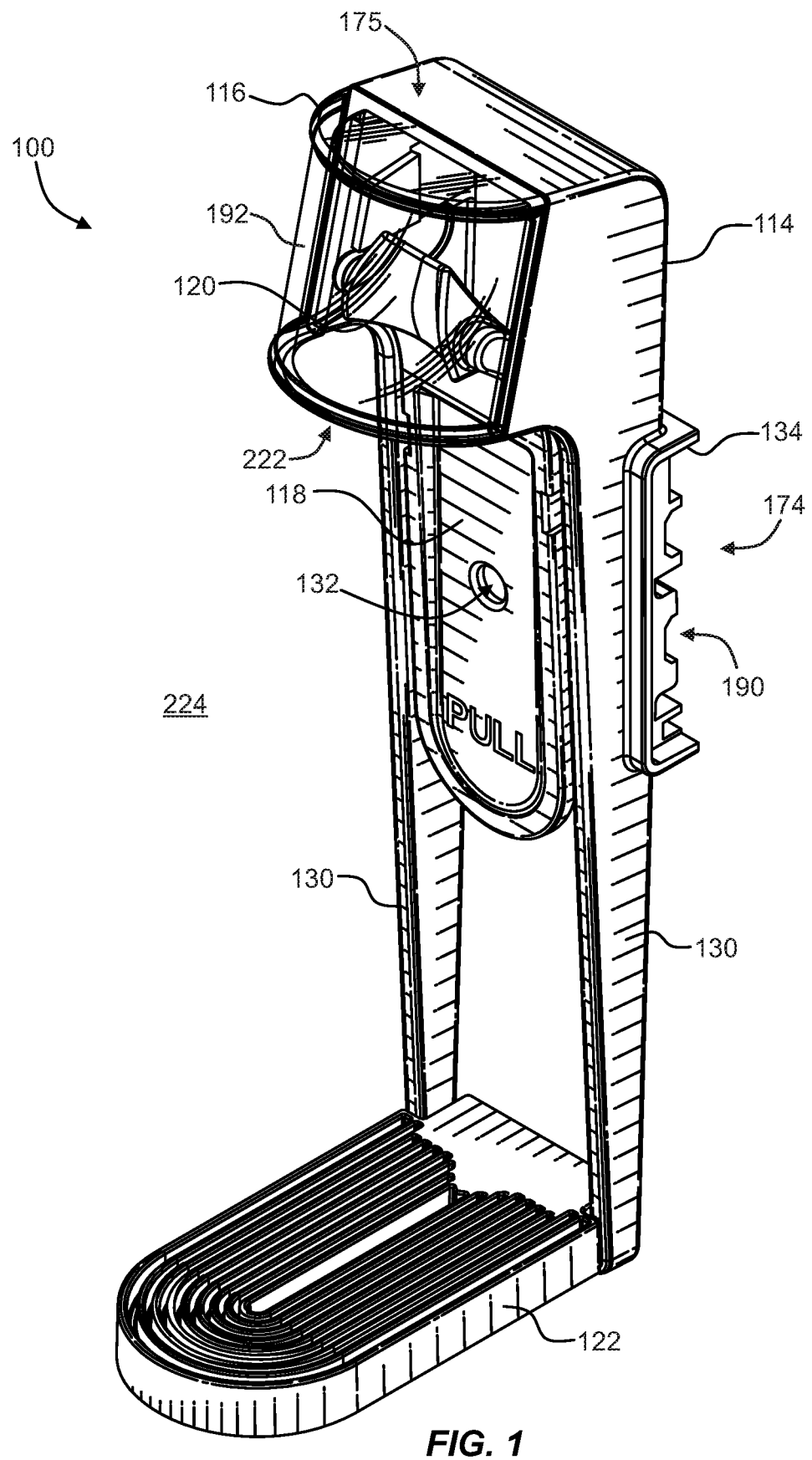
FIG. 1 is a diagrammatic perspective view of an example medical vial holder apparatus in accordance with the present disclosure.
Figure 2:
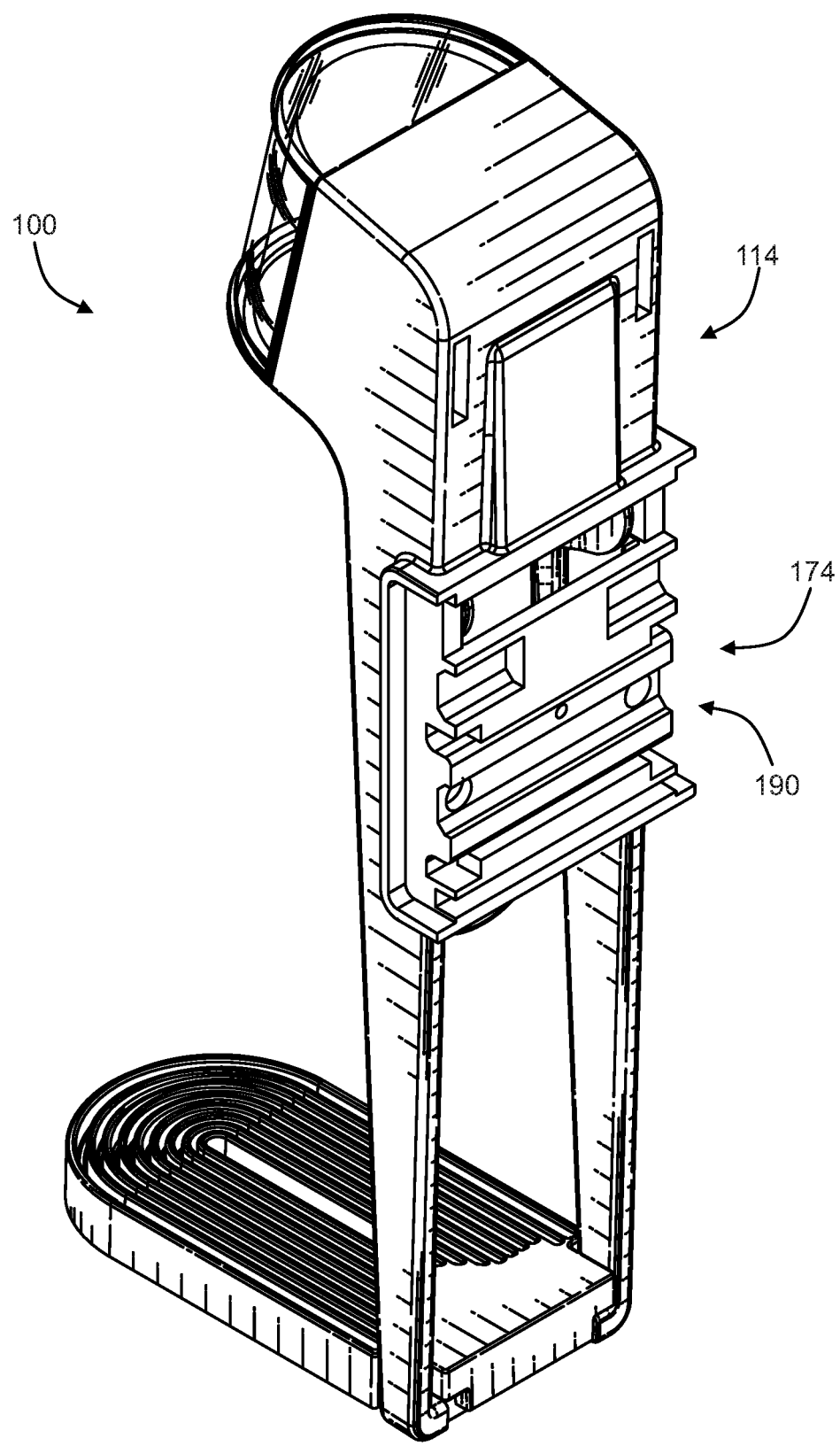
FIG. 2 is a further diagrammatic perspective view of the example medical vial holder apparatus of FIG. 1.

Referring now to the drawings, like reference numerals designate identical or corresponding features throughout the several views.

Referring to the various figures herein, one or more example embodiments of a medical vial holder apparatus in accordance with the present disclosure are shown at 100. As illustrated for example in FIGS. 24 and 25, an apparatus 100 and a mounting bracket assembly 102 may be combined to define a medical vial holder system 103.

Figure 10:
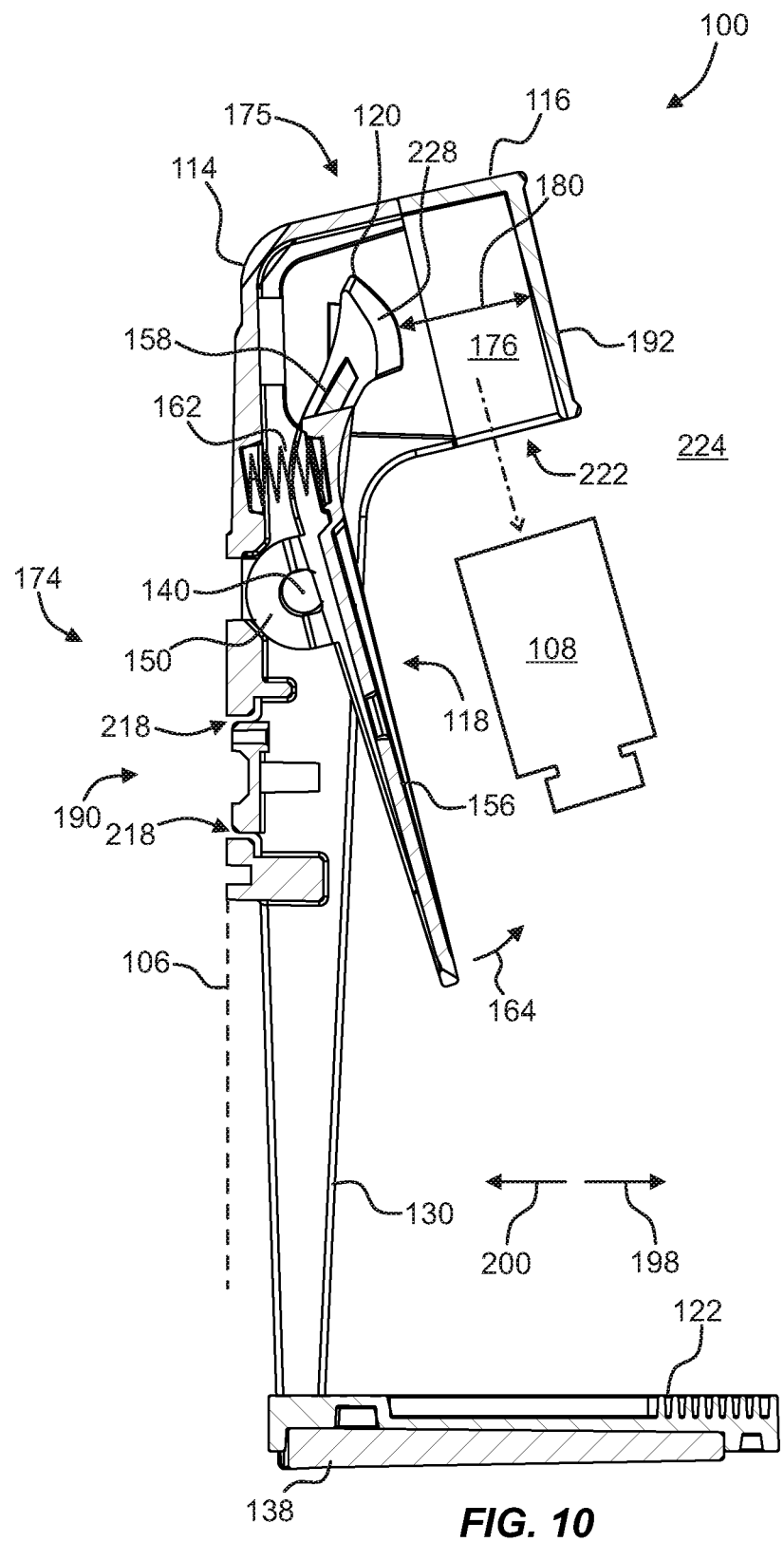
FIG. 10 is a diagrammatic perspective view similar to that of FIG. 9, but wherein the handle segment has been pulled in a pull direction to force the lever element to a release position, thereby allowing the medical vial to drop from the vial retention cavity and into the palm of the user pulling the handle segment.
Figure 11:
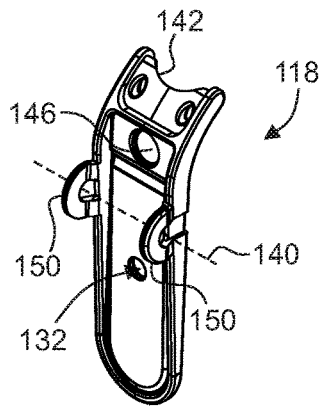
FIG. 11 is a diagrammatic perspective view of an example lever element in accordance with the present disclosure.
Figure 12:
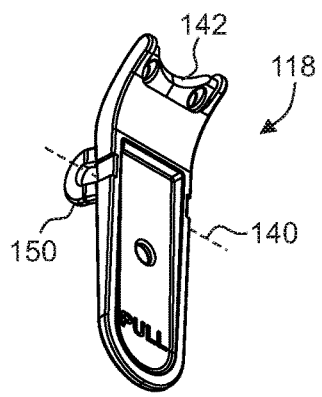
FIG. 12 is a further diagrammatic perspective view of the example lever element of FIG. 11.
Figure 18:
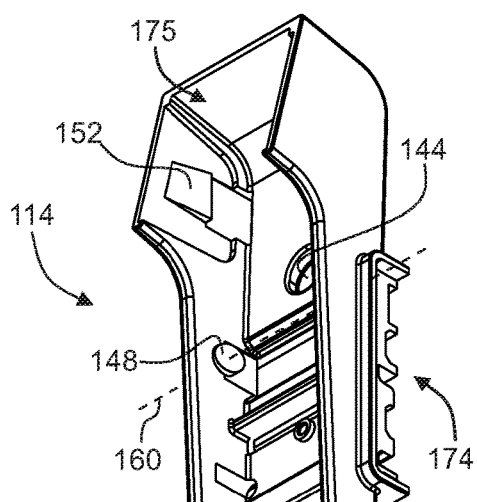
FIG. 18 is a diagrammatic perspective view of an example main body in accordance the present disclosure.
Figures 13, 14:
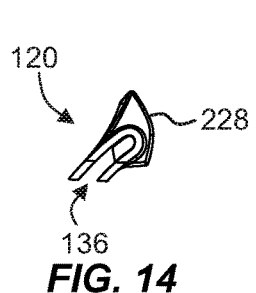
FIG. 13 is a diagrammatic perspective view of an example grip portion in accordance with the present disclosure.
FIG. 14 is a further diagrammatic side view of the example grip portion of FIG. 13.
Figure 15:
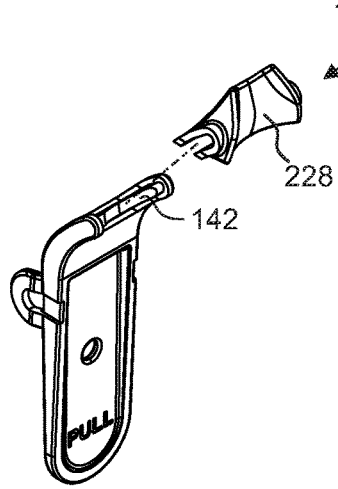
FIG. 15 is a diagrammatic perspective view of a lever element similar to that of FIG. 12, but wherein a grip portion is shown being made a portion of the lever element by way of mutual engagement between the attachment mouth of the grip portion and the engagement lip of the lever element.
Figure 16:
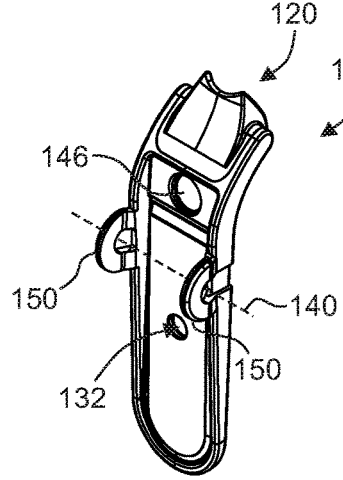
FIG. 16 is a diagrammatic perspective view of a lever element of FIG. 15, but with the grip portion installed.

Referring to FIGS. 8-10, the apparatus 100 may comprise a main body 114 having a mount engagement portion 174 and a vial engagement portion 175. A facing wall 192 may be attached to the vial engagement portion 175 thereby defining a vial retention cavity 176 therebetween. The vial retention cavity 176 may preferably be in communication with an external ambient environment 224 by way of a vial access port 222. A lever element 118 may be pivotally mounted to the main body 114 for pivotal movement of the lever element 118 between a grip position (see, for example, FIGS. 8-9) and a release position (see, for example, FIG. 10). The lever element 118 may have a grip portion 120 with a vial engagement face 228. A grip distance 180 may be defined between the vial engagement face 228 and the facing wall 192. Movement of the lever element 118 from the release position toward the grip position reduces the grip distance 180. In contrast, movement of the lever element 118 from the grip position toward the release position increases the grip distance 180. The lever element 118 may be resiliently biased toward the grip position. The resilient bias may be provided, for example, by a spring element 162. Referring to FIGS. 9, 11 and 18, respective ends of the spring element 162 may be retained by a first spring retention portion 144 of the main body 114 and a second spring retention portion 146 of the lever element 118.

Figure 17:
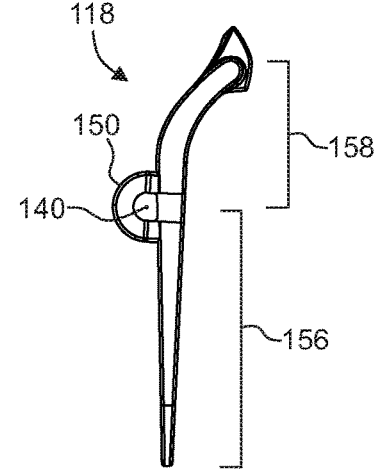
FIG. 17 is a diagrammatic side view of the example lever element of FIG. 16.
Figure 19:
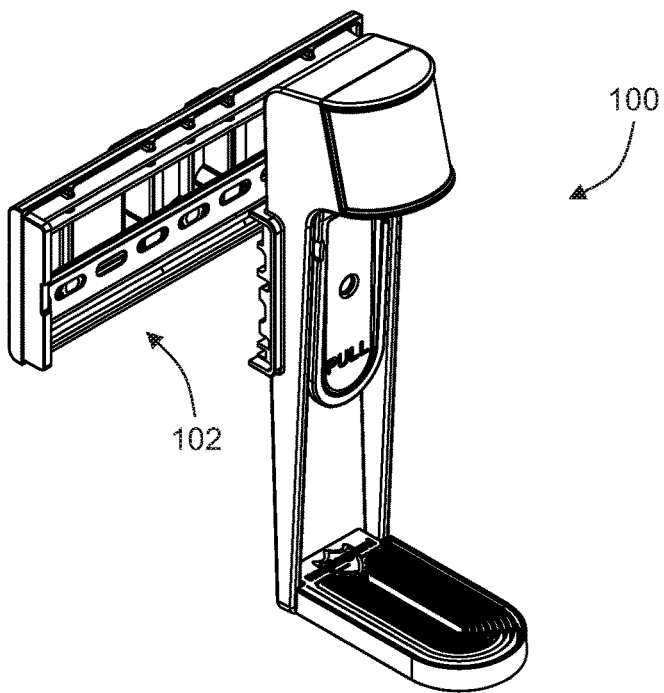
FIG. 19 is a diagrammatic perspective view of an example medical vial holder apparatus dismounted from a mounting bracket assembly.
Figure 20:
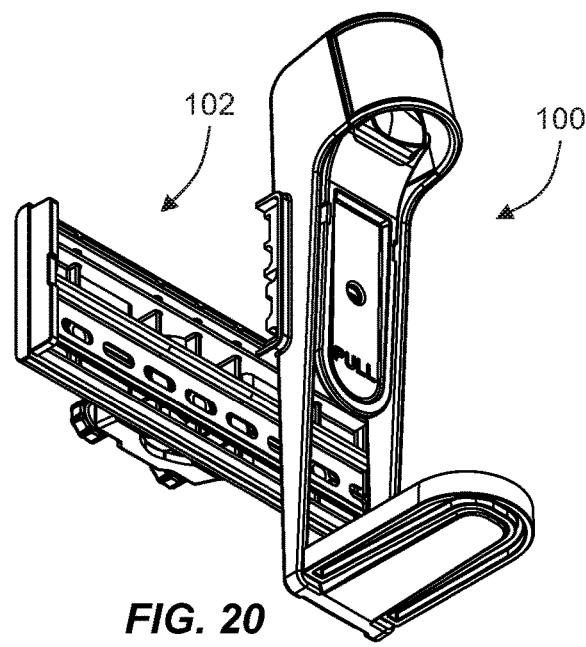
FIG. 20 is a further diagrammatic perspective view of the example medical vial holder apparatus and mounting bracket assembly shown in FIG. 19.
Figure 21:
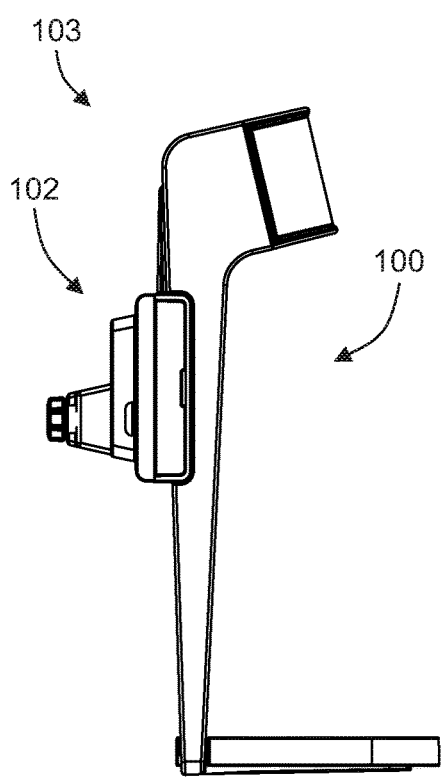
FIG. 21 is a diagrammatic side view of the example medical vial holder apparatus shown in FIG. 19, but wherein the example medical vial holder apparatus is shown mounted to the mounting bracket assembly to collectively form an example medical vial holder system.

Referring to FIG. 17, a lever element 118 may include a handle segment 156 and a grip segment 158 disposed on opposing sides of a lever axis 140. Referring to FIG. 10, the handle segment 156 may be configured to be pulled by a user (for example, in pull direction 164) to overcome the resilient bias and move the lever element 118 toward the release position. The grip portion 120 may be on the grip segment 158, and the pivotal movement may be about the lever axis 140. Referring to FIGS. 13-16, the lever element 118 may be formed (e.g., molded) with or have attached thereto the grip portion 120. If the lever element 118 and the grip portion 120 are initially formed separately, the lever element 118 may be formed with a grip engagement lip 142 configured to be received by an attachment mouth 136 of the grip portion 120. The grip portion 120 may preferably comprise a rubber or other high-friction material.

Referring to FIGS. 8-12 and 18, the lever element 118 may be pivotably mounted to the main body 114 such that pivotal movement of the lever element 118 corresponds to movement of the handle segment 156 in a pull direction 164 and a return direction 166. Such pivotal mounting may bring the lever axis 140 into axial alignment with the pivot axis 160 of the main body 114. For this purpose, the main body 114 may have a pair of first pivot engagement portions 148 configured to be engaged by corresponding second pivot engagement portions 150 of the lever element 118.

Referring to FIG. 8, in particular embodiments of the medical vial holder apparatus 100, the main body 114 may be elongated in parallel with a mounting axis 106. A vial retention axis 178 may be defined as extending from the vial retention cavity 176 through the vial access port 222. A vial retention angle 226 may be defined between the mounting axis 106 and the vial retention axis 178. The vial retention angle may be between 0 and 45 degrees, but is preferably between 10 degrees and 20 degrees. Even more preferably, the vial retention angle 226 may be between 10 and 15 degrees. Referring to FIG. 9, the apparatus 100 may be configured to grippingly retain an inverted medical vial 108 at least partially within the vial retention cavity 176 in alignment with the vial retention axis 178 when the lever element 118 is in a grip position. The top of the inverted medical vial 108 may thereby be exposed to be punctured by a needle of a syringe 220.

Figure 24:
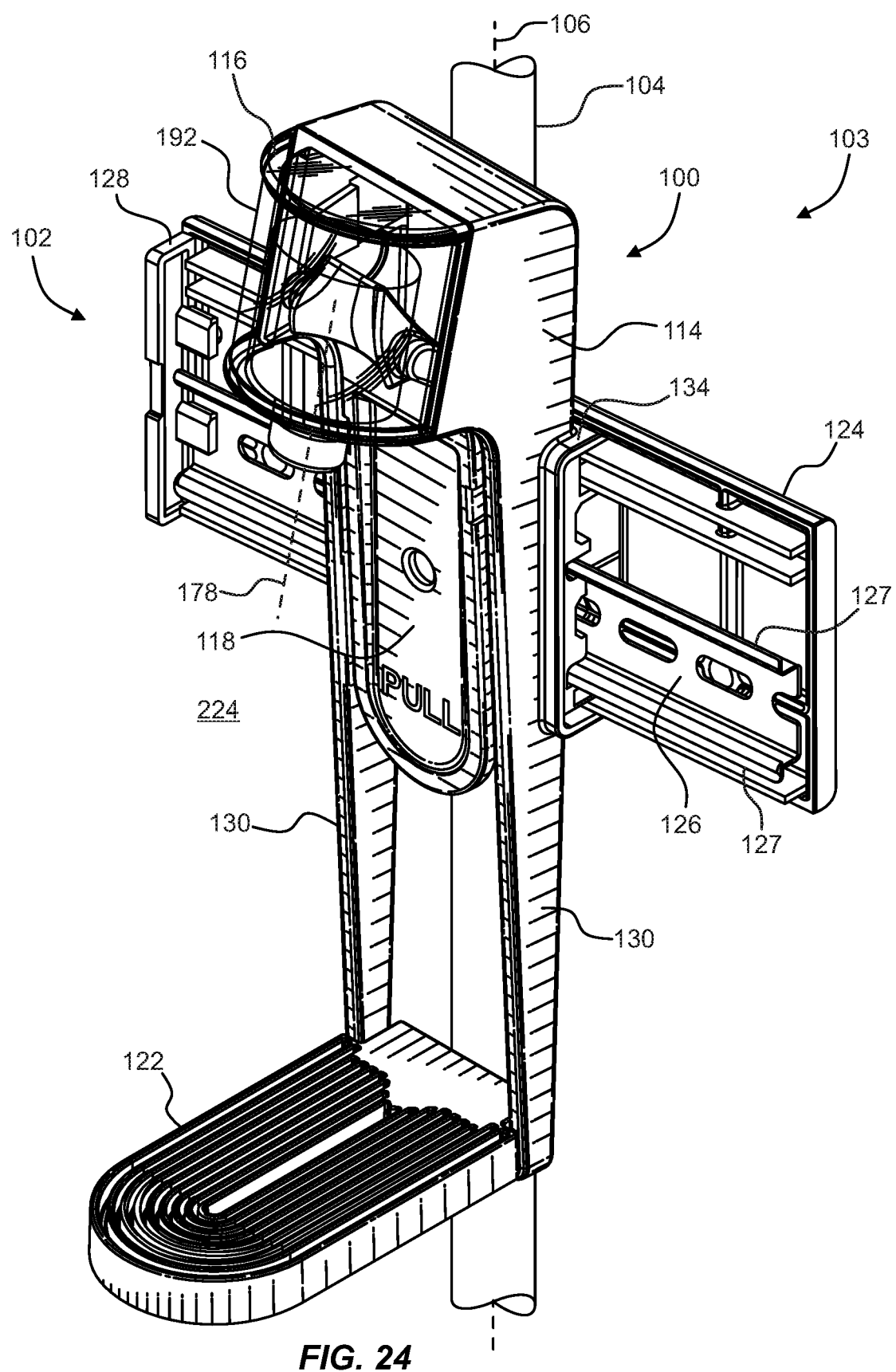
FIG. 24 is a diagrammatic perspective view of the example medical vial holder system of FIG. 22, but wherein the mounting bracket assembly has been adjustably secured on a mounting pole by way of pole securement hardware.

Referring to FIG. 24, in certain preferred embodiments of the apparatus 100 and system 103, the facing wall 192 may be curved, for example, about the vial retention axis 178. Moreover, the facing wall 192 may be opaque, or more preferably may be transparent.

Figure 23:
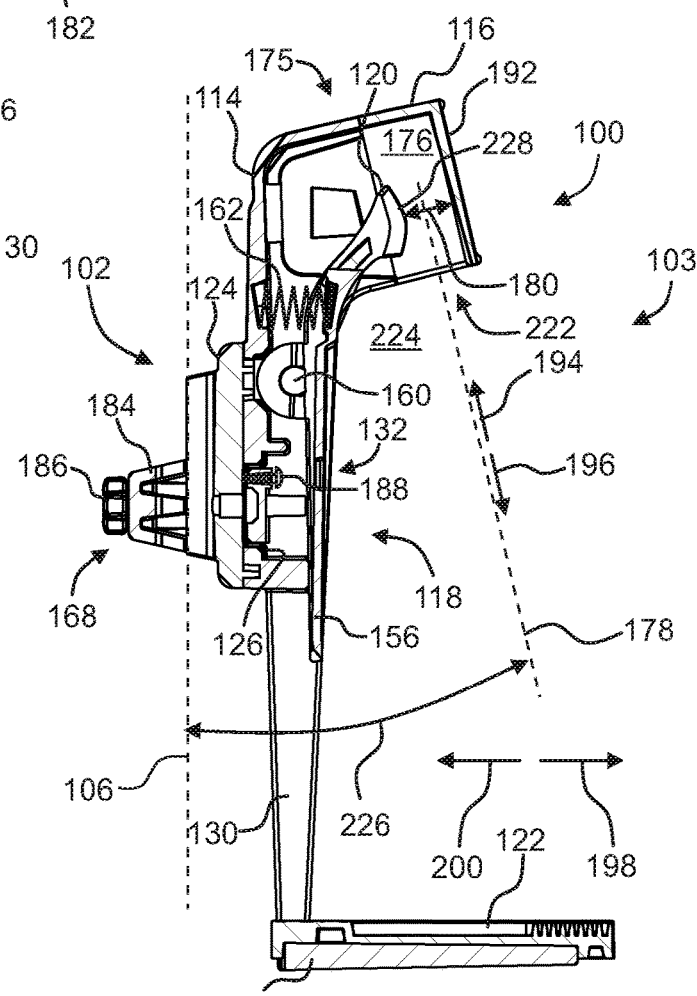
FIG. 23 is a diagrammatic cross-sectional view taken along lines 23-23 in FIG. 22.

Referring to FIGS. 8 and 23, in particular preferred embodiments of the apparatus 100 and system 103, the grip portion 120 may be disposed at least partially within the vial retention cavity 176.

Referring to FIGS. 8 and 9, in certain preferred embodiments of the apparatus 100 and system 103, the vial engagement face 228 may be configured to slidingly engage a medical vial 108 upon insertion of the medical vial into the vial retention cavity 176 and thereby cause an increase in the grip distance 180 during said insertion. Such configuration may involve curvature, chamfering or other shaping of the engagement face. By way of specific example, the vial engagement face 228 may have a compound curvature, as shown for example in FIGS. 13-15. An example of a vial insertion direction is shown at 194, and the corresponding vial removal direction is shown at 196. Moreover, a forward direction 198 and a rearward direction 200 with respect to the apparatus 100 are shown.

Referring to FIGS. 8 and 23, in particular preferred embodiments of the apparatus 100 and system 103, the apparatus 100 may further comprise a drip tray element 122. In such emblements, the handle segment 156 may be disposed between the vial retention cavity 176 and the drip tray element 122. The main body 114 may include a tray support element 138, which may be configured to removably support the drip tray element 122. The drip tray element 122 may be removably mountable to a tray support element 138. The drip tray element 122 may comprise a tray retention lip 170 and a tray alignment flange 172. In combination, these features may removably retain the drip tray element 122 on a tray support element 138 of the apparatus 100.

Figure 22:
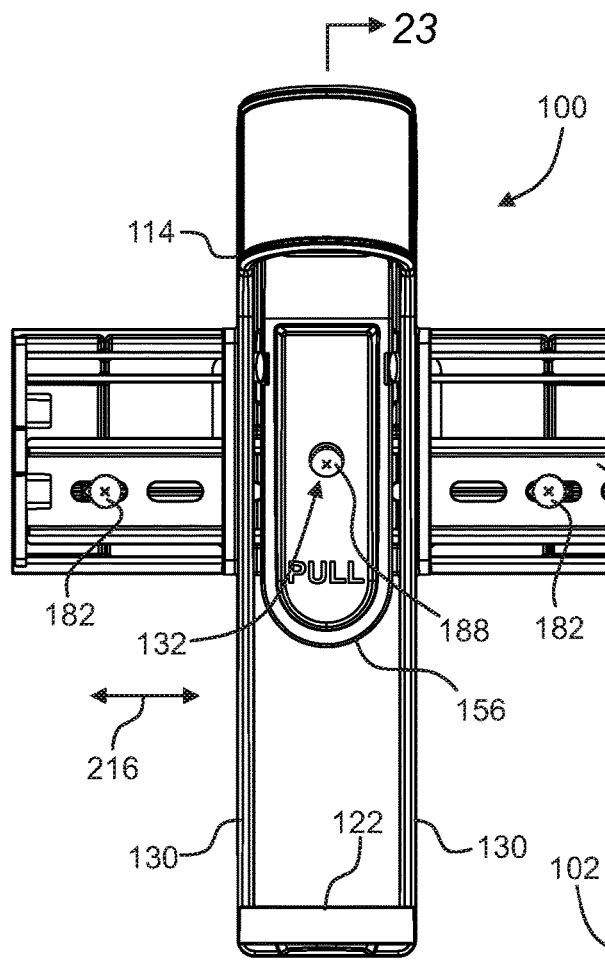
FIG. 22 is a diagrammatic front view of the example medical vial holder apparatus shown in FIG. 21.

Referring to FIGS. 18, 22 and 23, the main body 114 may include a pair of leg portions 130 laterally-spaced from one another and extending from the mount engagement portion 174 to the drip tray element 122. Referring to FIG. 22, in such embodiments, at least a portion of the handle segment 156 may be disposed between the pair of leg portions 130.

Referring to FIGS. 10, 23 and 24, in certain preferred embodiments of the apparatus 100 and system 103, the mount engagement portion 174 may include a rail engagement portion 190 configured to engage a mounting rail 126 (for example a din rail) having a pair of rail lips 127. The rail engagement portion 190 my have pair of rail grooves 218, each rail groove 218 being configured to slidably receive a corresponding one of said rail lips 127. Referring to FIG. 22, such configuration may allow an apparatus 100 to be selectively moved in a lateral direction 216 along the length of the mounting rail 126 until the apparatus 110 is secured at a particular lateral position along the mounting rail 126. Moreover, referring to FIGS. 22 and 23, in certain such apparatus 100 and system 103 embodiments, the apparatus 100 may further comprise a lateral alignment fastener 188 in the mount engagement portion 174. The lateral alignment fastener 188 may be configured to be transported (for example, threadedly) into and out of locking engagement with the mounting rail 126. When the lateral alignment fastener 188 is transported into the locking engagement, the main body 114 may be prevented from sliding along the mounting rail 126. The handle segment 188 may include an access aperture 132 therethrough. As illustrated for example in FIG. 22, the access aperture 132 may be in accessing alignment with the lateral alignment fastener 188.

Referring to FIGS. 10, 23 and 24, in certain preferred embodiments of the apparatus 100 and system 103, the facing wall 192 may be part of a window element 116. In such embodiments, the main body 114 may include a pair of first window securement portions 152, the window element 116 may include a pair of second window securement portions 154, and the second window securement portions 154 may be configured to engage the first window securement portions 152 to secure the window element 116 to the main body 114. Referring to FIGS. 34 and 38-40, the second window securement portions 154 may each include a window securement aperture 155. In such embodiments, the window securement apertures 15 may each be in receiving engagement with a respective one of said first window securement portions 152 when the window element 116 is secured to the main body 114. The window element 116 may preferably be partially or entirely transparent, so that a vial label 110 may be visible from a viewpoint 112 outward of the window element 116 when a medical vial 108 is inserted into and retained within the vial retention cavity 176.

Figure 34:
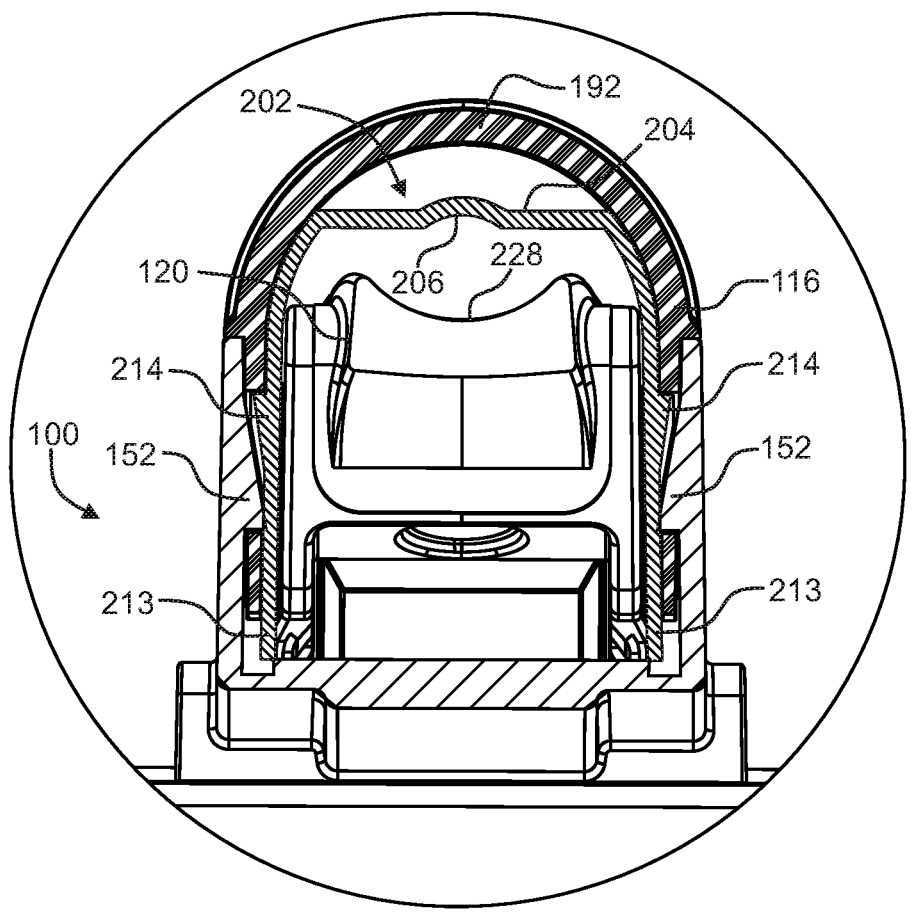
FIG. 34 is a cross-sectional view taken along lines 34-34 of FIG. 33.
Figure 35:
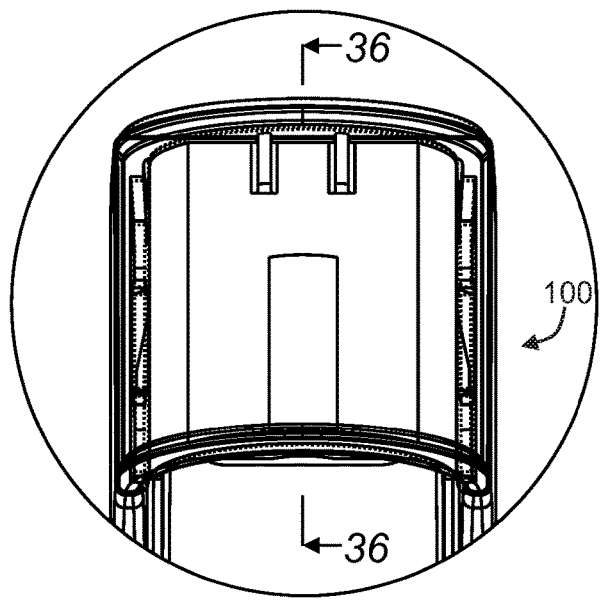
FIG. 35 is a further diagrammatic detail view of the portion of the medical vial holder system of FIG. 29, but shown from a front angle.
Figure 36:
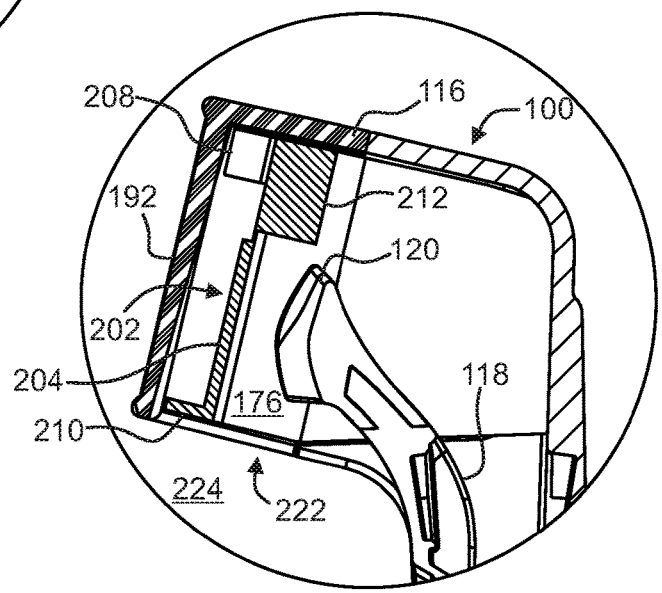
FIG. 36 is a cross-sectional view taken along lines 36-36 of FIG. 35.

As illustrated for example, in FIGS. 34 and 38, the first window securement portions 152 may be each be ramped to facilitate placement of the window securement apertures 155 into the aforementioned receiving engagement with the first window securement portions 152. Moreover, the second window securement portions 154 may be configured to be elastically deformed by the first window securement portions 152 during the facilitated placement, and return to undeformed state once the window securement apertures 155 are in the receiving engagement. For example, the second window securement portions 154 may be configured to be temporarily forced (e.g., flexed) toward one another during attachment or removal of the window element 116 from the vial engagement portion 175, either by a user or by sliding engagement between the second window securement portions 154 and the first window securement portions 152.

Figure 31:
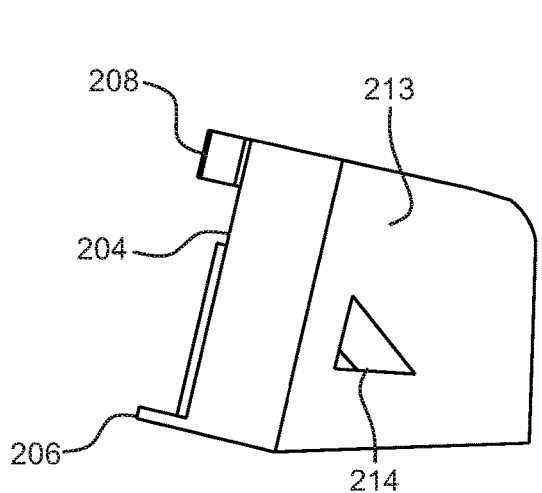
FIG. 31 is a diagrammatic side view of one example of a vial size adaptor in accordance with the present disclosure.
Figure 32:
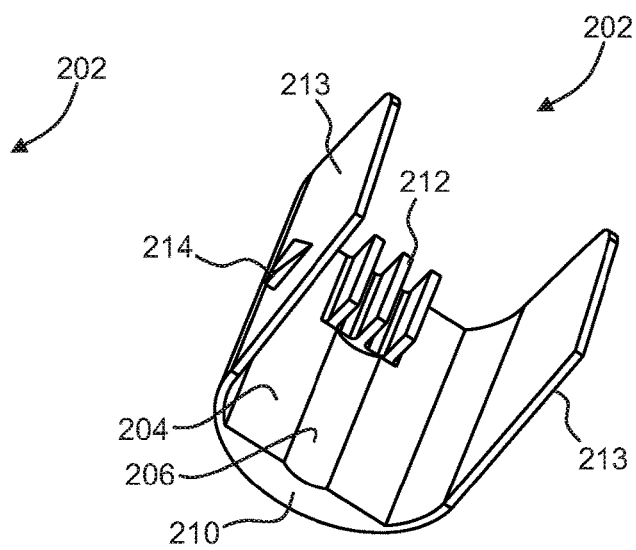
FIG. 32 is a diagrammatic perspective view of the example vial size adaptor of FIG. 31.
Figure 33:
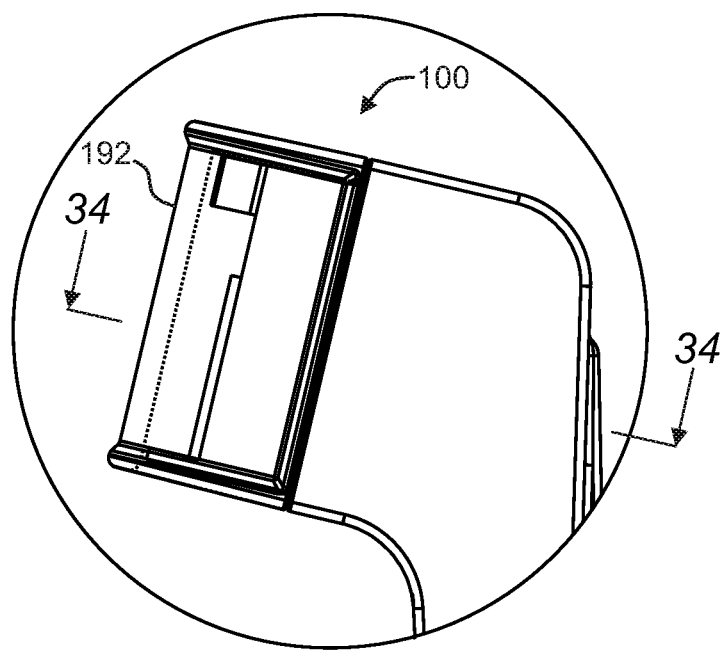
FIG. 33 is a further diagrammatic detail view of the portion of the medical vial holder system of FIG. 29, but shown from a side angle.
Figure 37:
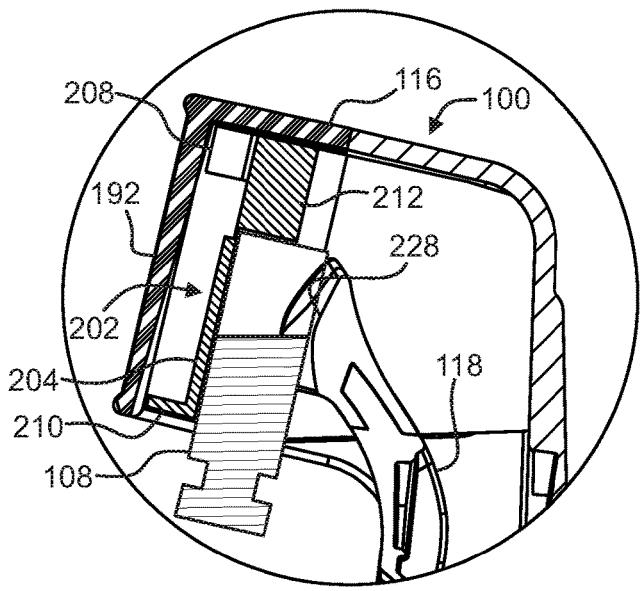
FIG. 37 is a cross-sectional view similar to that of FIG. 36, but wherein an inverted 1 ml medical vial is shown grippingly retained within the vial retention cavity of the apparatus between the vial engagement face of the grip portion and the offset wall of the vial size adaptor.

Referring to FIGS. 28-37, in particular preferred embodiments of the apparatus 100 and system 103, the medical vial holder apparatus 100 may further comprise a vial size adaptor 202 configured to be fixedly retained within the vial retention cavity 176. The vial size adaptor 202 may include an offset wall 204. Referring to FIGS. 34 and 37, the offset wall 204 may be configured to be disposed between the facing wall 192 and the vial engagement face 228 when the vial size adaptor 202 is in the fixed retention within the vial retention cavity 176. The vial size adaptor 202 may include a lower offset member 210 and an upper offset member 208. The lower offset member 210 and the upper offset member 208 may be affixed to the offset wall 204 and may be configured to engage the facing wall 192 when the vial size adaptor is in the aforementioned fixed retention. Additionally or in the alternative, referring for example to FIGS. 36-37, the vial size adaptor 202 may include a vial insert detent member 212 configured to limit upward travel of a medical vial 108 within the vial retention cavity 176 when the vial size adaptor 202 is in the fixed retention. Referring to FIGS. 32 and 34, the offset wall 204 may include a vial alignment channel 206 for aiding in aligning a medical vial 108 within the vial retention cavity 176.

Referring to FIGS. 31-32 and 34, a vial size adaptor 202 may include a pair of adaptor securement portions 213. In such embodiments, when the vial size adaptor 202 is in said fixed retention, the offset wall 204 may be disposed between the facing wall 192 and the vial engagement face 228, and the grip portion 120 may be disposed between the adaptor securement portions 213. The adaptor securement portions 213 may each include an adaptor securement boss 214. Each of the adaptor securement bosses 214 may be configured to be in received engagement with a respective one of the window securement apertures 155 when the vial size adaptor 202 is in the aforementioned fixed retention. As illustrated doer example in FIGS. 28, 32 and 34, the adaptor securement bosses 214 may each be ramped to facilitate positioning of the vial size adaptor 202 into the fixed retention. The adaptor securement portions 213 may be configured to be elastically deformed by engagement between the adaptor securement bosses 214 and the second window securement portions 154 during the facilitated positioning, may be configured to return to undeformed state once the adaptor securement bosses 214 are in the received engagement with the window securement apertures 155.

Referring to FIGS. 22-25, a medical vial holder system 103 may comprise a mounting rail 126 having a pair of rail lips 127, and a plurality of medical vial holder apparatuses 100. The pair of rail grooves 218 of each of the medical vial holder apparatuses 100 may be in receipt of the pair of rail lips 127. Each of the medical vial holder apparatuses 100 may comprise a lateral alignment fastener 188 in the mount engagement portion 174. The lateral alignment fasteners 188 may be configured to be transported (for example, threadedly) into and out of locking engagement with the mounting rail 126, thereby preventing the main body 114 of each of the medical vial holder apparatuses 100 from sliding along the mounting rail. The handle segment 156 of each of the medical vial holder apparatuses 100 may include an access aperture 132 therethrough. The access apertures 132 may be in accessing alignment with the respective lateral alignment fasteners 188. For example, in embodiments in which the lateral alignment fasteners 188 are screws, the access apertures 132 may allow a user to insert a torqueing tool (such as a screwdriver) through the access aperture 132 to engage the head of the lateral alignment fastener 188 to facilitate transport thereof into and out of the locking engagement.

Figure 3:
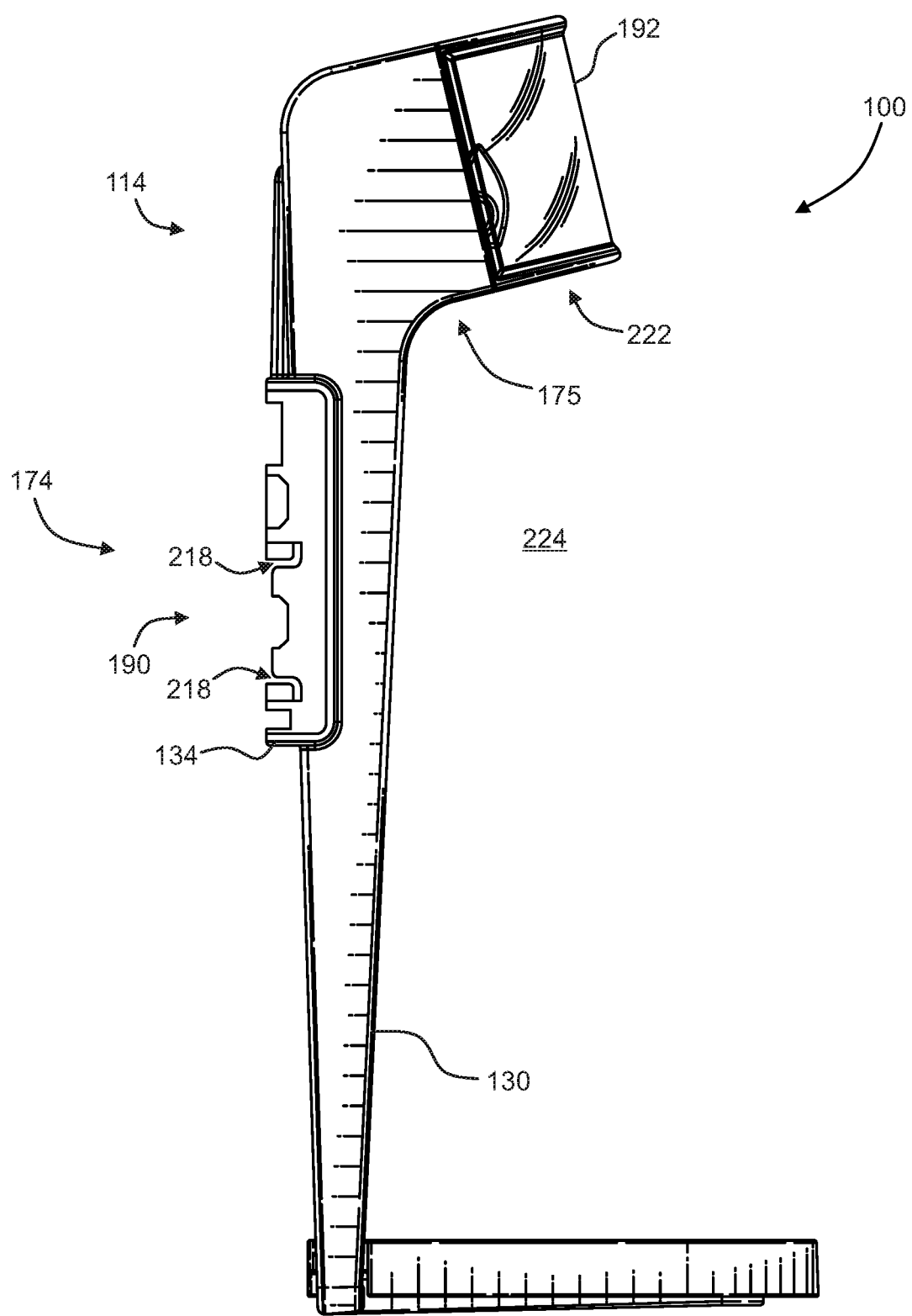
FIG. 3 is a diagrammatic side view of the example medical vial holder apparatus of FIG. 1.
Figure 4:
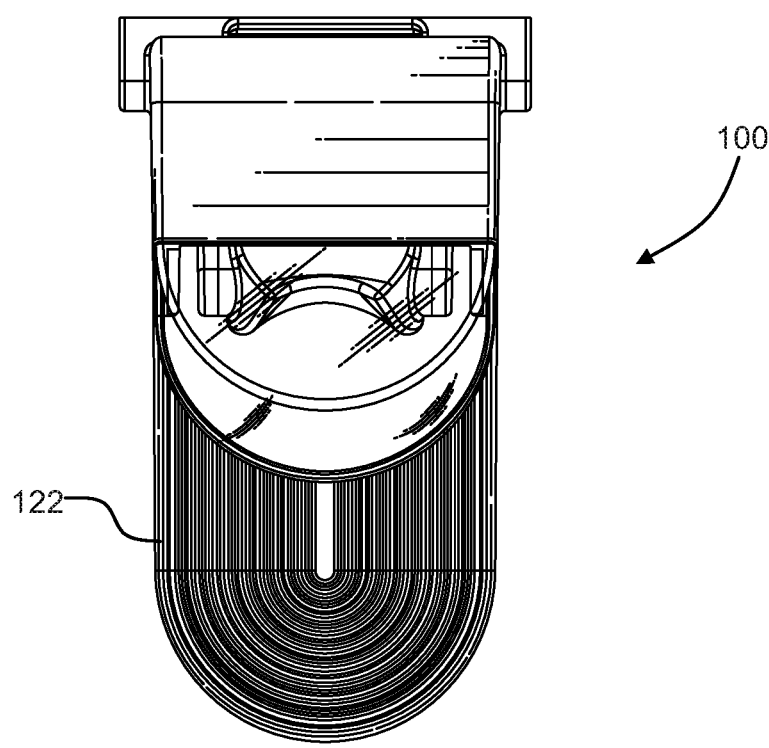
FIG. 4 is a diagrammatic top view of the example medical vial holder apparatus of FIG. 1.
Figure 5:
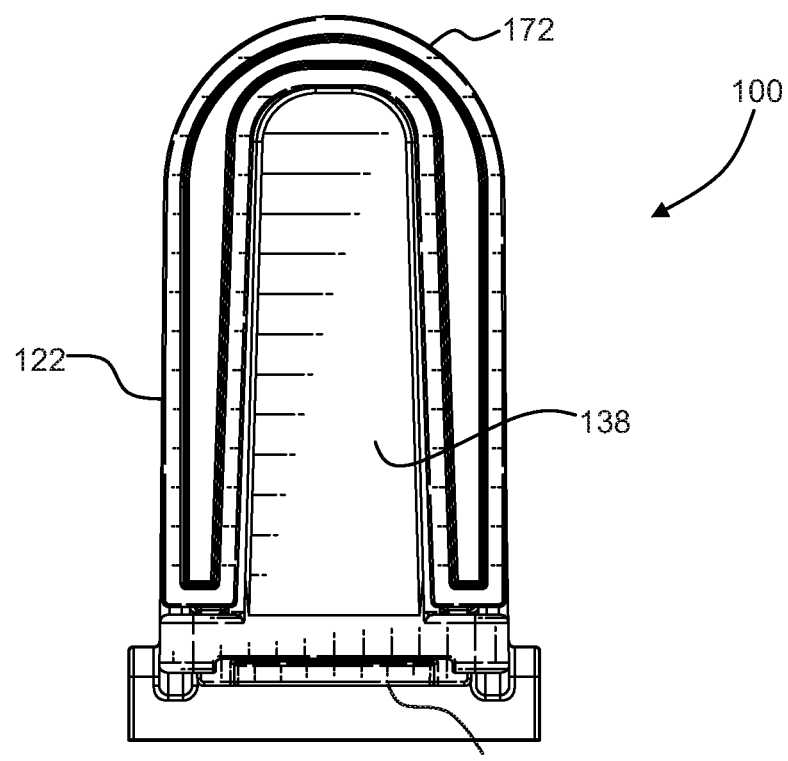
FIG. 5 is a diagrammatic bottom view of the example medical vial holder apparatus of FIG. 1.
Figure 6:
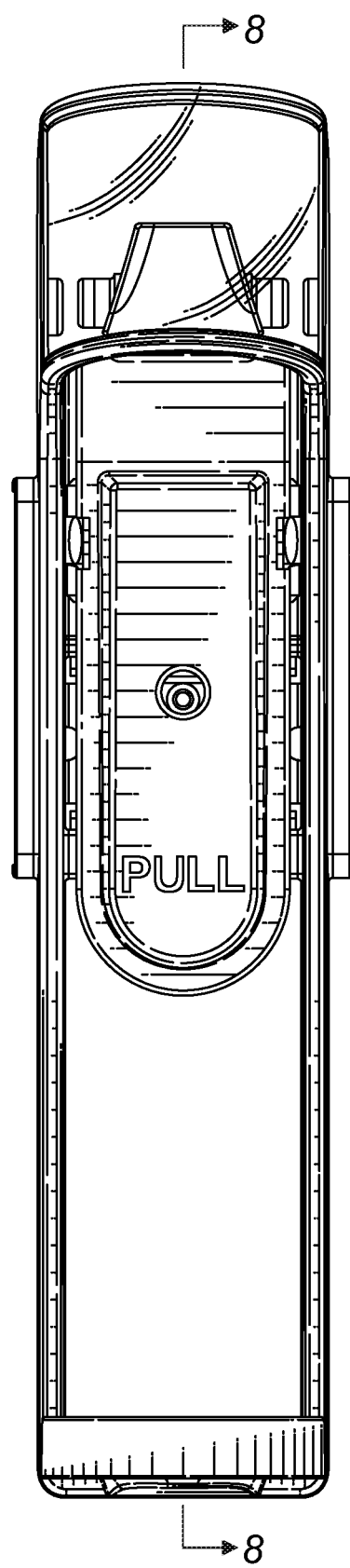
FIG. 6 is a diagrammatic front view of the example medical vial holder apparatus of FIG. 1.
Figure 7:
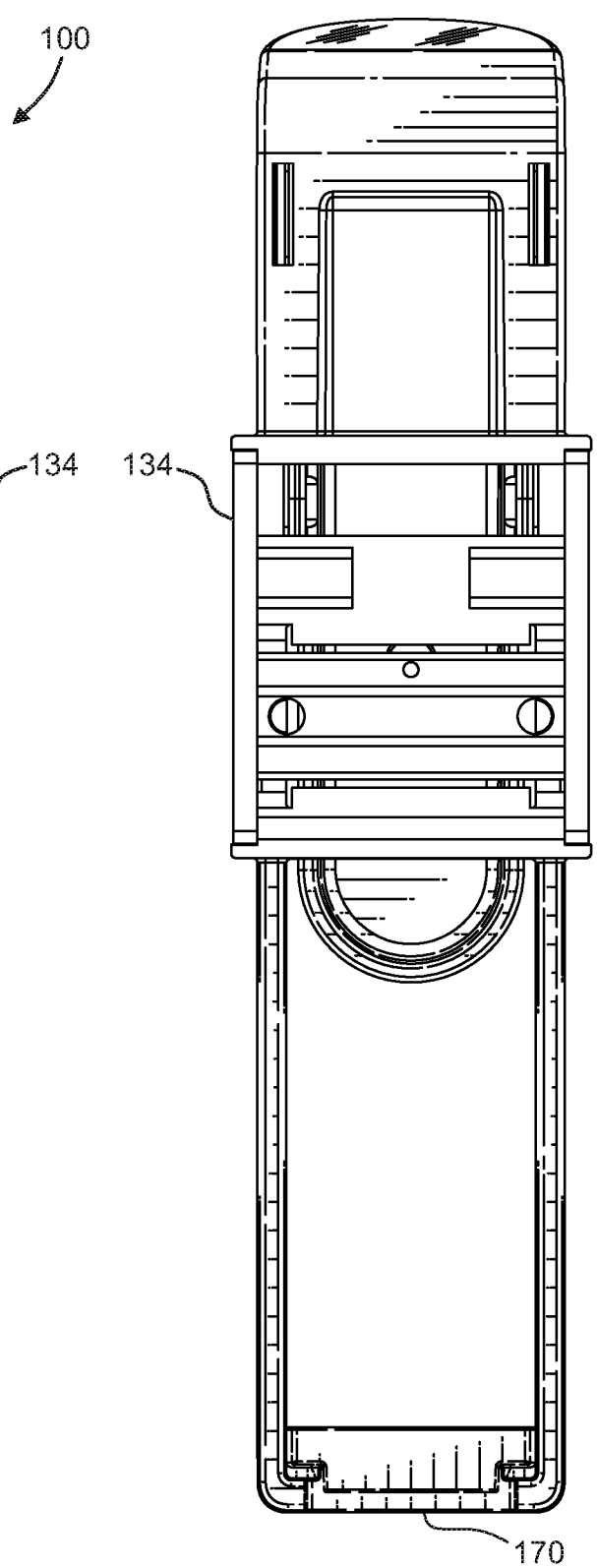
FIG. 7 is a diagrammatic rear view of the example medical vial holder apparatus of FIG. 1.
Figure 27:
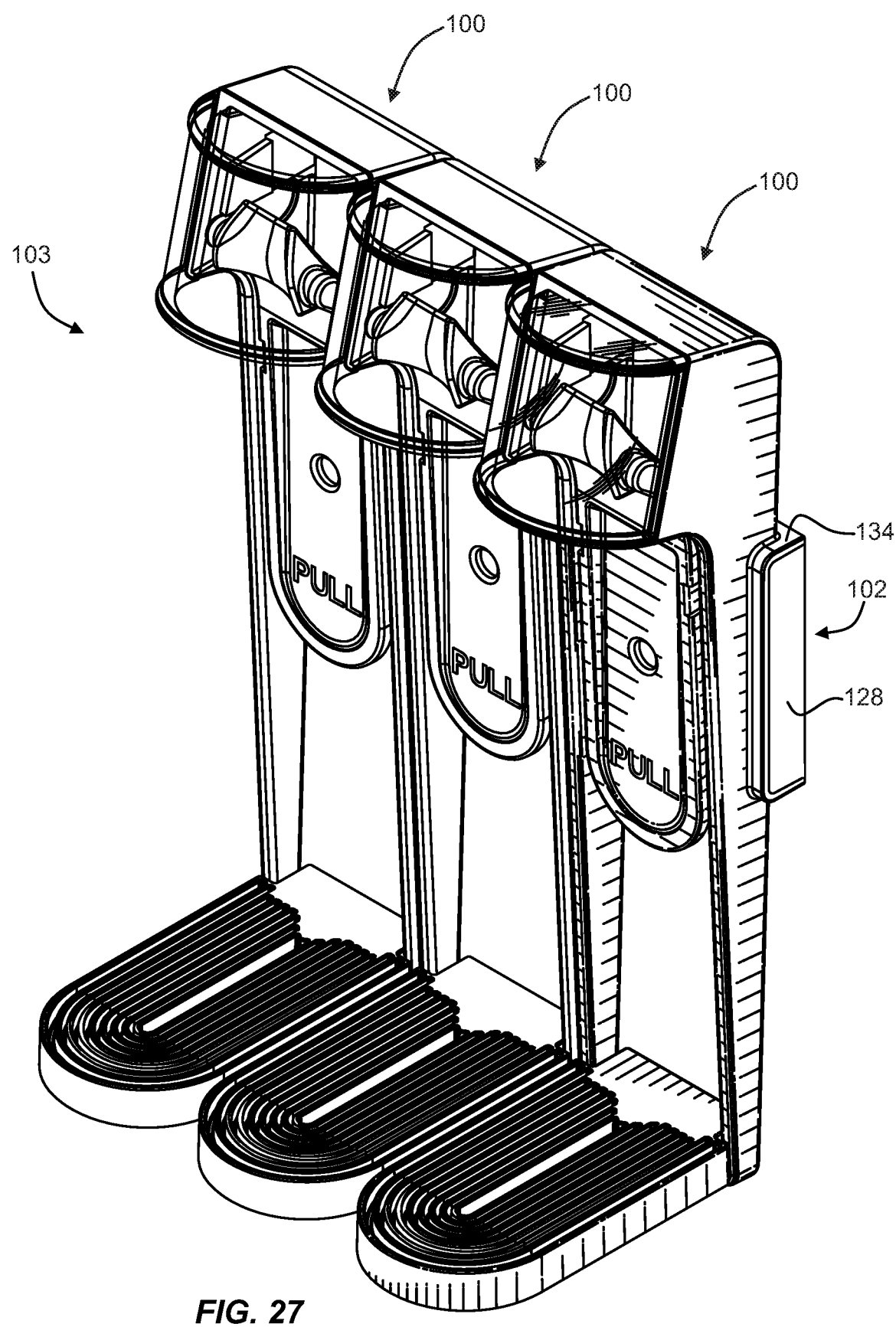
FIG. 27 is a diagrammatic perspective view of an example medical vial holder system in accordance with the present disclosure, illustrating how a plurality of medical vial holder apparatuses may be mounted to a single mounting bracket assembly, which may in turn be secured to a single mounting pole.
Figure 28:
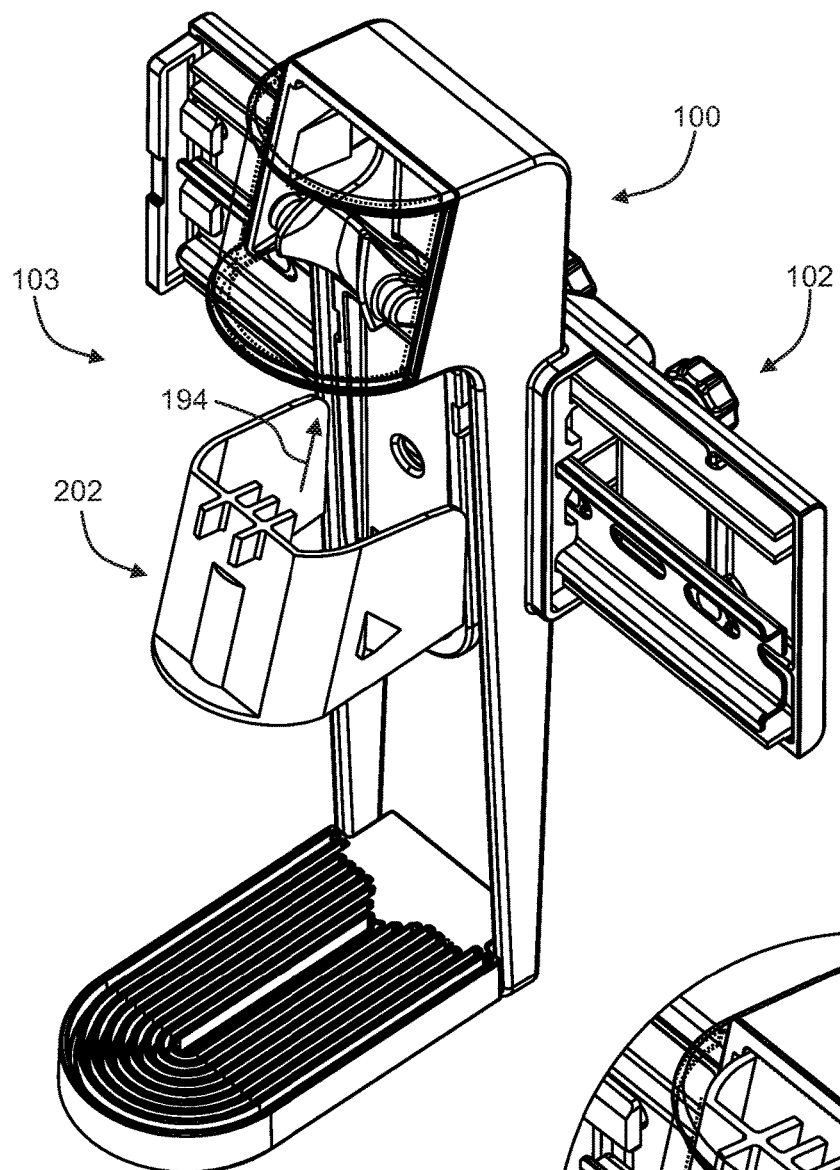
FIG. 28 is a diagrammatic perspective view of an example medical vial holder system in accordance with the present disclosure, illustrating a vial size adaptor being inserted into the vial retention cavity to be fixedly retained therein.
Figure 29:
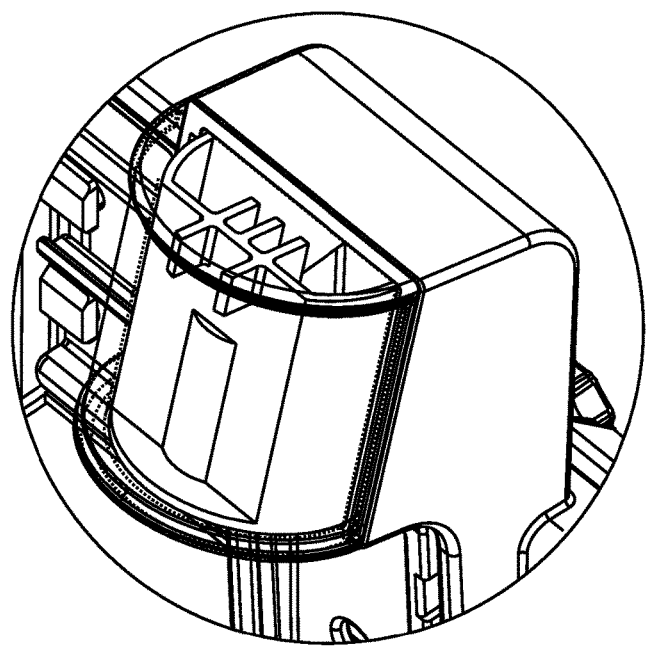
FIG. 29 is a diagrammatic detail view of a portion of the medical vial holder system of FIG. 28, but wherein the vial size adaptor is shown fixedly retained within the vial retention cavity.
Figure 30:
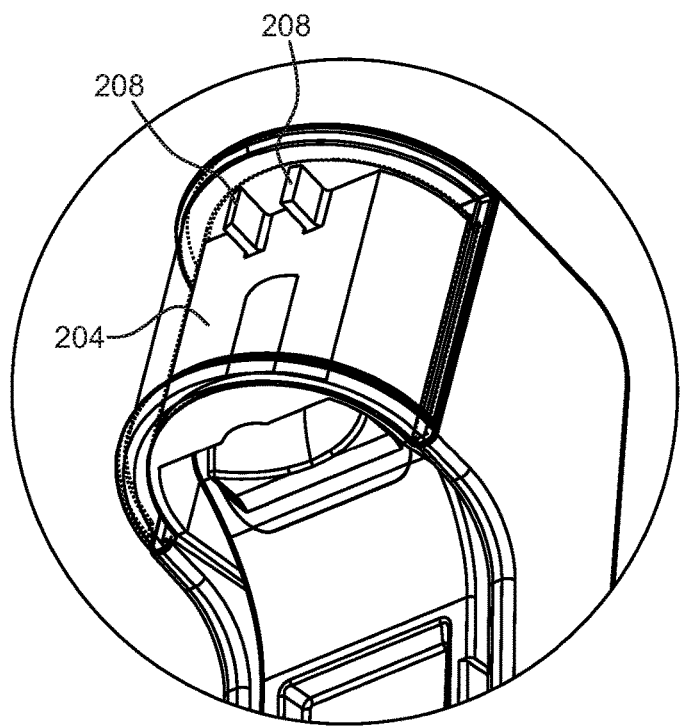
FIG. 30 is a further diagrammatic detail view of the portion of the medical vial holder system of FIG. 29, but shown from another angle.

Referring to FIGS. 22-25, in particular embodiments of a medical vial holder system 103, the mounting rail 126 may be attached to a mounting base 124 to collectively form part of a mounting bracket assembly 102. Such attachment may be by way of, for example, rail fasteners 182. The rail fasteners 182 may be, for example, screws. Referring to FIGS. 3, 24 and 27, the mount engagement portion 174 of each medical vial holder apparatus 100 may include a mounting flange 134 to align with corresponding features of the mounting base 124 and with mounting flanges 134 of directly adjacent apparatuses 100. Moreover, the mounting bracket assembly 102 may include a pair of end cover elements 128, one installed at each end of the mounting bracket assembly 102.

Figure 25:
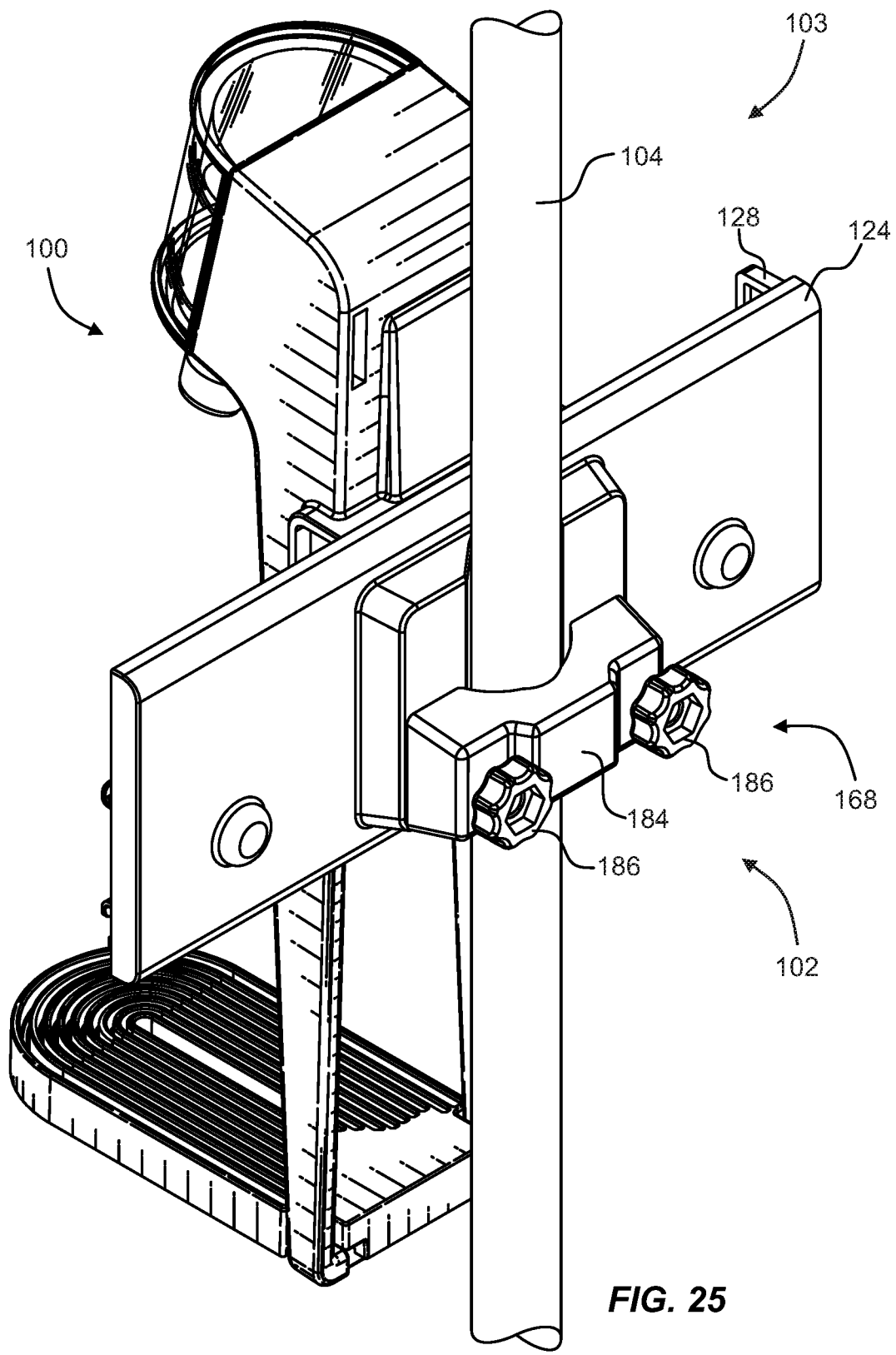
FIG. 25 is a further diagrammatic perspective view of the example medical vial holder apparatus of FIG. 24.
Figure 26:
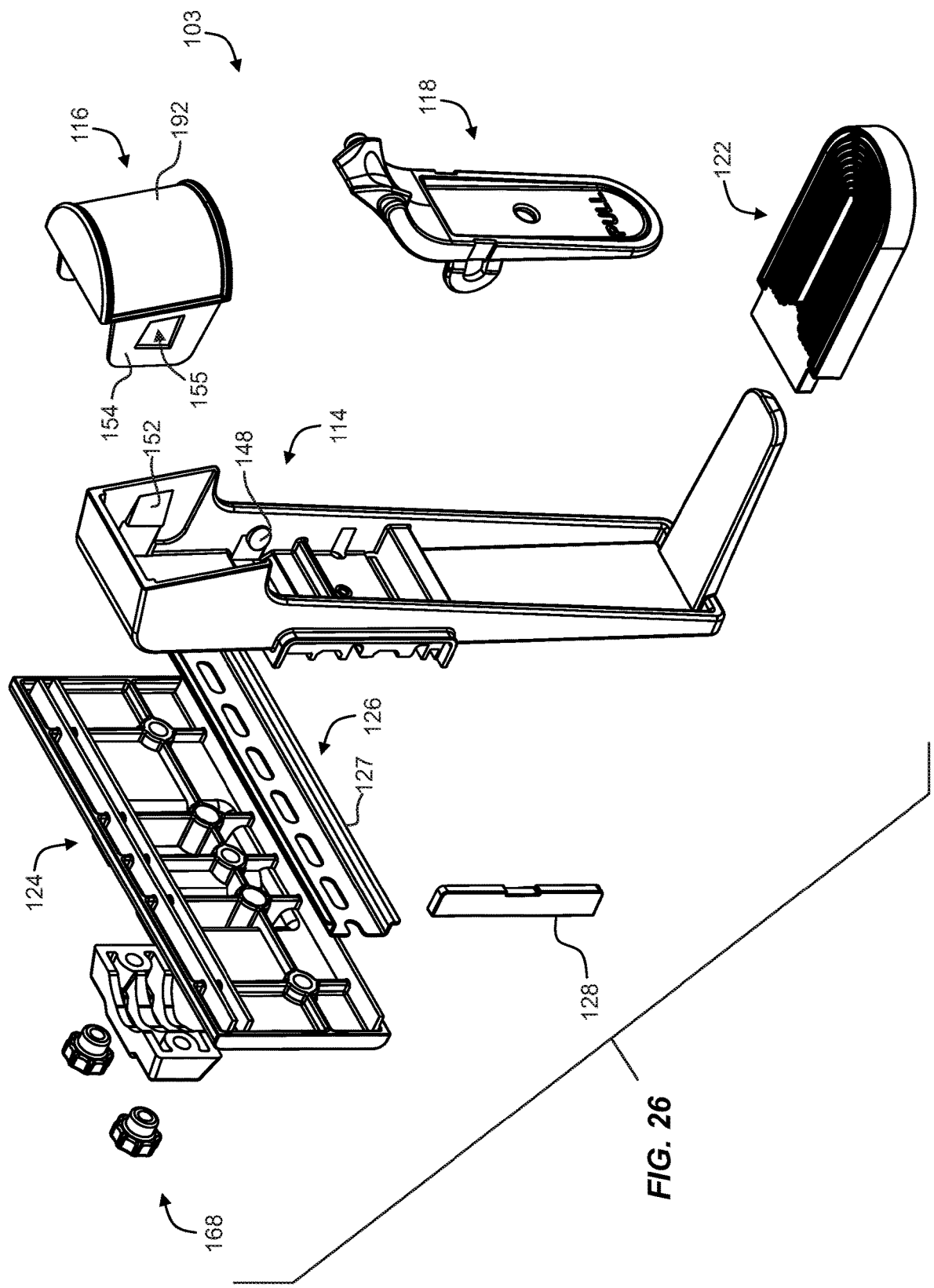
FIG. 26 is a diagrammatic exploded view of portions of the example medical vial holder system of FIG. 24, illustrating example embodiments of various potential components thereof.

The mounting bracket assembly 102 may include pole securement hardware 168 configured to secure the mounting bracket assembly 102 to a mounting pole 104, such as a standard IV pole commonly found in a medical treatment environment. In such case, the pole securement hardware 168 may also allow adjustment of a vertical position of the mounting bracket assembly 102 (and thus the entire system 103) along the mounting pole 104. Referring to FIG. 25, the pole securement hardware 168 may include a pole clamp element 184 and one or more manually-actuatable clamp fasteners 186. In an alternate system 103, the mounting rail 126 may be fastened directly to a wall within a medical treatment environment, rather than to a mounting base 124.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A medical vial holder apparatus comprising:
   a main body having a mount engagement portion and a vial engagement portion;
   a facing wall attached to the vial engagement portion thereby defining a vial retention cavity therebetween, the vial retention cavity being in communication with an external ambient environment by way of a vial access port; and
   a lever element being pivotally mounted to the main body for pivotal movement of the lever element between a grip position and a release position, the lever element having a grip portion with a vial engagement face, a grip distance being defined between the vial engagement face and the facing wall;
   wherein movement of the lever element from the release position toward the grip position reduces the grip distance, and movement of the lever element from the grip position toward the release position increases the grip distance; and
   wherein the lever element is resiliently biased toward the grip position.

2. The medical vial holder apparatus as defined in claim 1, wherein the lever element includes a handle segment and a grip segment disposed on opposing sides of a lever axis, wherein
   (a) the handle segment is configured to be pulled by a user to overcome the resilient bias and move the lever element toward the release position;
   (b) the grip portion is on the grip segment; and
   (c) the pivotal movement is about the lever axis.

3. The medical vial holder apparatus as defined in claim 2, wherein
   (a) the main body is elongated in parallel with a mounting axis;
   (b) a vial retention axis is defined as extending from the vial retention cavity through the vial access port;
   (c) a vial retention angle is defined between the mounting axis and the vial retention axis, the vial retention angle being between 10 degrees and 20 degrees; and
   (d) the apparatus is configured to grippingly retain an inverted medical vial at least partially within the vial retention cavity in alignment with the vial retention axis when the lever element is in the grip position.

4. The medical vial holder apparatus as defined in claim 3, wherein the facing wall is curved about the vial retention axis.

5. The medical vial holder apparatus as defined in claim 4, wherein the facing wall is opaque.

6. The medical vial holder apparatus as defined in claim 4, wherein the facing wall is transparent.

7. The medical vial holder apparatus as defined in claim 2, wherein the grip portion is disposed at least partially within the vial retention cavity.

8. The medical vial holder apparatus as defined in claim 1, wherein the vial engagement face is configured to slidingly engage a medical vial upon insertion of the medical vial into the vial retention cavity and thereby cause an increase in the grip distance during said insertion.

9. The medical vial holder apparatus as defined in claim 8, wherein the vial engagement face has a compound curvature.

10. The medical vial holder apparatus as defined in claim 1, wherein the resilient bias is provided by a spring element.

11. The medical vial holder apparatus as defined in claim 2 further comprising a drip tray element, and wherein the handle segment is disposed between the vial retention cavity and the drip tray element.

12. The medical vial holder apparatus as defined in claim 11, wherein the main body includes a pair of leg portions laterally-spaced from one another and extending from the mount engagement portion to the drip tray element.

13. The medical vial holder apparatus as defined in claim 12, wherein at least a portion of the handle segment is disposed between the pair of leg portions.

14. The medical vial holder apparatus as defined in claim 11, wherein the main body includes a tray support element, the tray support element being configured to removably support the drip tray element.

15. The medical vial holder apparatus as defined in claim 1, wherein the mount engagement portion includes a rail engagement portion configured to engage a mounting rail having a pair of rail lips, the rail engagement portion having pair of rail grooves, each rail groove being configured to slidably receive a corresponding one of said rail lips.

16. The medical vial holder apparatus as defined in claim 15 further comprising a lateral alignment fastener in the mount engagement portion, wherein (a) the lateral alignment fastener is configured to be threadedly transported into and out of locking engagement with the mounting rail; and
(b) when the lateral alignment fastener is threadedly transported into the locking engagement, the main body is prevented from sliding along the mounting rail.

17. The medical vial holder apparatus as defined in claim 16, wherein the handle segment includes an access aperture therethrough, the access aperture being in accessing alignment with the lateral alignment fastener.

18. The medical vial holder apparatus as defined in claim 1, wherein
(a) the facing wall is part of a window element;
(b) the main body includes a pair of first window securement portions;
(c) the window element includes a pair of second window securement portions; and
(d) the second window securement portions are configured to engage the first window securement portions to secure the window element to the main body.

19. The medical vial holder apparatus as defined in claim 18, wherein
(a) the second window securement portions each include a window securement aperture; and
(b) the window securement apertures are each in receiving engagement with a respective one of said first window securement portions when the window element is secured to the main body.

20. The medical vial holder apparatus as defined in claim 19, wherein the first window securement portions are each ramped to facilitate placement of the window securement apertures into said receiving engagement.

21. The medical vial holder apparatus as defined in claim 20, wherein the second window securement portions are configured to
(a) be elastically deformed by the first window securement portions during the facilitated placement; and
(b) return to undeformed state once the window securement apertures are in the receiving engagement.

22. The medical vial holder apparatus as defined in claim 1 further comprising a vial size adaptor configured to be fixedly retained within the vial retention cavity, the vial size adaptor including an offset wall;
wherein the offset wall is disposed between the facing wall and the vial engagement face when the vial size adaptor is in said fixed retention.

23. The medical vial holder apparatus as defined in claim 22, wherein the vial size adaptor includes a lower offset member and an upper offset member, the lower offset member and the upper offset member being affixed to the offset wall and being configured to engage the facing wall when the vial size adaptor is in said fixed retention.

24. The medical vial holder apparatus as defined in claim 22, wherein the vial size adaptor includes a vial insert detent member configured to limit upward travel of a medical vial within the vial retention cavity when the vial size adaptor is in the fixed retention.

25. The medical vial holder apparatus as defined in claim 22, wherein the offset wall includes a vial alignment channel for aligning a medical vial within the vial retention cavity.

26. The medical vial holder apparatus as defined in claim 19 further comprising a vial size adaptor configured to be fixedly retained within the vial retention cavity, the vial size adaptor including an offset wall and a pair of adaptor securement portions;
wherein when the vial size adaptor is in said fixed retention,
(a) the offset wall is disposed between the facing wall and the vial engagement face; and
(b) the grip portion is disposed between the adaptor securement portions.

27. The medical vial holder apparatus as defined in claim 26, wherein the adaptor securement portions each include an adaptor securement boss, each of the adaptor securement bosses being configured to be in received engagement with a respective one of said window securement apertures when the vial size adaptor is in said fixed retention.

28. The medical vial holder apparatus as defined in claim 27, the adaptor securement bosses are each ramped to facilitate positioning of the vial size adaptor into said fixed retention.

29. The medical vial holder apparatus as defined in claim 20, wherein the adaptor securement portions are configured to
(a) be elastically deformed by engagement between the adaptor securement bosses and the second window securement portions during the facilitated positioning; and
(b) return to undeformed state once the adaptor securement bosses are in the received engagement.

30. A medical vial holder system comprising:
a mounting rail having a pair of rail lips; and
a plurality of medical vial holder apparatuses as defined in claim 15, the pair of rail grooves of each of the medical vial holder apparatuses being in receipt of the pair of rail lips.

31. The medical vial holder system as defined in claim 30, wherein
(a) each of the medical vial holder apparatuses comprise a lateral alignment fastener in the mount engagement portion;
(b) the lateral alignment fasteners are configured to be threadedly transported into and out of locking engagement with the mounting rail; and
(c) when the lateral alignment fasteners are threadedly transported into the locking engagement, the main body of each of the medical vial holder apparatuses is prevented from sliding along the mounting rail.

32. The medical vial holder system as defined in claim 31, wherein the handle segment of each of the medical vial holder apparatuses includes an access aperture therethrough, the access apertures being in accessing alignment with the respective lateral alignment fasteners.

33. The medical vial holder system as defined in claim 31, wherein the mounting rail is attached to a mounting base to collectively form part of a mounting bracket assembly, the mounting bracket assembly including pole securement hardware configured to secure the mounting bracket assembly to a mounting pole and allow adjustment of a vertical position of the mounting bracket assembly along the mounting pole.

* * * * *